United States Patent
Sarig et al.

(10) Patent No.: US 7,733,214 B2
(45) Date of Patent: Jun. 8, 2010

(54) SYSTEM AND METHODS FOR THE REMOTE MEASUREMENT OF A PERSON'S BIOMETRIC DATA IN A CONTROLLED STATE BY WAY OF SYNCHRONIZED MUSIC, VIDEO AND LYRICS

(75) Inventors: Amnon Sarig, Woodland Hills, CA (US); Ran Cohen, Tel Aviv (IL)

(73) Assignee: Tune Wiki Limited, Tortola (VG)

( * ) Notice: Subject to any disclaimer, the term of this patent is extended or adjusted under 35 U.S.C. 154(b) by 255 days.

(21) Appl. No.: 12/099,194

(22) Filed: Apr. 8, 2008

(65) Prior Publication Data

US 2009/0051487 A1 Feb. 26, 2009

Related U.S. Application Data

(63) Continuation-in-part of application No. 12/017,389, filed on Jan. 22, 2008.

(60) Provisional application No. 60/957,220, filed on Aug. 22, 2007.

(51) Int. Cl.
G05B 19/00 (2006.01)
(52) U.S. Cl. ................................... 340/5.52
(58) Field of Classification Search ................ 340/5.52, 340/573.1, 539.11, 825.69; 455/3.01; 707/10
See application file for complete search history.

(56) References Cited

U.S. PATENT DOCUMENTS

| 7,468,032 | B2 * | 12/2008 | Stahmann et al. | 600/301 |
|---|---|---|---|---|
| 2005/0123886 | A1 | 6/2005 | Hua et al. | |
| 2007/0242040 | A1 | 10/2007 | Ullrich et al. | |
| 2008/0139889 | A1 * | 6/2008 | Bagan | 600/300 |
| 2009/0105548 | A1 * | 4/2009 | Bart | 600/300 |
| 2009/0205042 | A1 * | 8/2009 | Zhou et al. | 726/19 |

FOREIGN PATENT DOCUMENTS

EP 1830347 A1 9/2007

OTHER PUBLICATIONS

"Evil Lyrics FAQ" Internet Article, [Online] May 24, 2005, pp. 1-33, XP002529750 Retrieved from the Internet: URL:http://www.evil-labs.sk/evillyrics/faq/faq.php> [retrieved on May 26, 2009].
Egidi L et al: "Entertainment everywhere - Bringing multimedia contents into MP3 files" IEEE Communications Magazine, IEEE Service Center, Piscataway, US, vol. 43, No. 5, May 1, 2005, pp. 90-97, XP011134850 ISSN: 0163-6804.
Paul McFedries: "Technically Speaking: It's a Wiki, Wiki World" IEEE Spectrum, IEEE Inc. New York, US, vol. 43, No. 12, 1 Dec. 2006, pp. 88-88, XP011144743 ISSN: 0018-9235.
European Search Report and Annex to the European Search Report May 28, 2009.

* cited by examiner

*Primary Examiner*—Phung Nguyen
(74) *Attorney, Agent, or Firm*—Naomi Assia Law Offices

(57) ABSTRACT

A method enabling a user with an electronic communication device to establish and stabilize his mental, emotional and physical condition in response to stimulation data and then using biometric sensors applied to the user to provide for remote/local gathering of standardized biometric data into a remote database coordinated with remote server software via an electronic network. The method includes initiating a session and selecting a session type by the user. The method also includes loading a track with the stimulation data, establishing links to the biometric sensors, setting the timing tolerances and biometric parameters based on new or existing user rules, stimulating the user with at least one of visual, audio, lyrics, text and vibration tracks to elicit stimulation data from the user, recording time stamps corresponding to key/tap input, deriving sync relationship between the user and the stimulation data, waiting for the variance and biometric parameters to stabilize and displaying a depiction of the stabilized condition on a screen.

7 Claims, 2 Drawing Sheets

SYSTEM AND METHODS FOR THE REMOTE MEASUREMENT OF A PERSON'S BIOMETRIC DATA IN A CONTROLLED STATE BY WAY OF SYNCHRONIZED MUSIC, VIDEO AND LYRICS

CROSS-REFERENCE TO RELATED APPLICATION

This application is a continuation-in-part of co-pending U.S. patent application Ser. No. 12/017,389, filed Jan. 22, 2008, entitled "A System and Method for Real Time Local Music Playback and Remote Server Lyric Timing Synchronization Utilizing Social Networks and Wiki Technology," which is assigned to the assignee of the present patent application, and is incorporated herein by reference, and which claims priority from U.S. patent application 60/957,220, filed Aug. 22, 2007, entitled "System and Method for Real Time Local Music Playback and Remote Server Lyric Timing Synchronization Utilizing Social Networks and Wiki Technology".

FIELD OF THE INVENTION

The present invention relates generally to synchronization data gathering, and more particularly to a method for remotely deriving time stamped synchronization data that allows for a relationship between two or more data sources to be established consciously, subconsciously or unconsciously.

BACKGROUND OF THE INVENTION

The validity of biometric data is affected by the emotional, mental and physical condition of a subject when biometric data is gathered. Data validity is further adversely affected by variables in the subject's surroundings and any recent activity.

Remote, automated gathering of biometric data allows for the creation of large databases at low cost. Such databases have great immediate value to the user by providing the source biometric data and longer term value for the larger medical community for research and reference.

Thus, it would be advantageous to provide a source of biometric data having long term value for the larger medical community for research and reference.

SUMMARY OF THE INVENTION

Accordingly, it is a principal object of the present invention to provide a source of biometric data having long term value for the larger medical community for research and reference.

It is another principal object of the present invention to provide a method that allows a user to establish and stabilize his mental, emotional and physical condition, and once this has been achieved to provide for remote or local gathering of standardized biometric data for the user.

It is one other principal object of the present invention to enable a user to interact with software that provides audio/video stimulation to the user and allows timing data feedback, whereby the user taps an input device. Biometric sensors gather data for blood pressure, heart rate, breathing and perspiration, for example. As the user settles into a normal meditative state the data will stabilize.

A method enabling a user with an electronic communication device to establish and stabilize his mental, emotional and physical condition in response to stimulation data and then using biometric sensors applied to the user to provide for remote/local gathering of standardized biometric data into a remote database coordinated with remote server software via an electronic network. The method includes initiating a session and selecting a session type by the user. The method also includes loading a track with the stimulation data, establishing links to the biometric sensors, setting the timing tolerances and biometric parameters based on new or existing user rules, stimulating the user with at least one of visual, audio, lyrics, text and vibration tracks to elicit stimulation data from the user, recording time stamps corresponding to key/tap input from the user, deriving the sync relationship between the user and the stimulation data, waiting for any sync variance and the biometric parameters to stabilize and displaying a depiction of the stabilized condition on a screen of the user's electronic communication device.

The data from the first session or sessions allows the central servers software to establish a normal data-set for that user, which then allows for the establishment of baseline biometric limits for that user.

The lyrics word searches are limited to songs that are on hand to do this, because it is necessary to have material to play back. Optionally, a link can be provided to the "track preview" feature on the Amazon music store, for example, and there the track can be purchased for implementation according to the method of the present invention.

When data from subsequent sessions is uploaded to the centralized database it may be used to monitor the health of the user by referencing this new data against the previously established baseline data for that user. If during a session the users cardiac data values start to go 'out of limits,' for example, then an audio/video message is sent recommending that the user seek medical advice.

The opportunity for advertising exists during the data gathering sessions by insertion of splash pages or audio messages into the meditation sequence.

A mobile phone, or other appropriate handheld device, equipped with biometric data gathering software allows for the remote real-time gathering of normalized biometric data as outlined above. The opportunity exists for the creation of large data-sets containing biometric data relating to the health of a user, including details of age, sex, nationality, weight, lifestyle and other parameters. Due to the ease and low cost of data gathering and the large potential size of such data-sets, statistical analysis will allow for a high degree of accuracy of databases generated using this approach.

The present invention provides for a handheld digital device that allows for the local derivation of synchronization data for a user that describes a relationship between two or more real time data streams, consciously or unconsciously, and for the uploading of this synchronization data to a remote database where it may be utilized by other users.

A session is initiated by a user with a device such as an Internet enabled mobile phone. In its simplest configuration the mobile phone would also have a heart rate monitor connected. The user contacts the Internet based session server and chooses a generic session style, for example, health, social, recuperation or exercise. A user choosing health would then select a subcategory, for example, cardiac monitoring.

The software program displays a visual stimulation pattern on the screen in the form of a video, words, text and/or lyrics that relate to an audio file that is played over the mobile phones headphones or speaker.

The user's heart rate is continuously monitored by the server side program. As the session progresses the user taps a key, or, if the handheld device has one, a touch sensitive screen in synchronization with the session's audio and visual stimulation. If the device has a vibration capability then this stimulus may be used as well. A time stamp is recorded for each user tap.

The program stimulates in a known and controllable way all the primary senses of the user, while minimizing the background influences of the surroundings and any relevant recent activity and emotional experiences. As the session progresses the program monitors and compares the timing variations between the users tapped in time stamp data and the session's stimulation data. At the start of a session the variances will be high. As the program progresses the variances are reduced until it reaches a plateau.

Once this plateau has been reached, the users biometric data will have stabilized to within their own personal norms. This calming of biometric functions is similar to the result of the waiting and resting time doctors often impose on patients when taking blood pressure measurements. However, it is more extensive and is actually beneficial to the health of the individual. It has certain similarities to meditation.

Once the time data variance plateau has been reached and the users biometric data has stabilized, the biometric data can be compared with data from previous sessions for that user. Analysis of this data will allow the program to inform the user of his progress in improving biometric functions and to alert him of any problems that may require further diagnosis by his doctor.

The implementation described here uses a mobile phone as an example. However, a suitably equipped personal computer connected to the Internet, a handheld remote control for a cable or satellite television receiver which has Internet connectivity could be utilized as well.

There has thus been outlined, rather broadly, the more important features of the invention in order that the detailed description thereof that follows hereinafter may be better understood. Additional details and advantages of the invention will be set forth in the detailed description, and in part will be appreciated from the description, or may be learned by practice of the invention.

BRIEF DESCRIPTION OF THE DRAWINGS

For a better understanding of the invention with regard to the embodiments thereof, reference is now made to the accompanying drawings, in which like numerals designate corresponding elements or sections throughout, and in which.

DETAILED DESCRIPTION OF A PREFERRED EMBODIMENT

The principles and operation of a method and an apparatus according to the present invention may be better understood with reference to the drawings and the accompanying description, it being understood that these drawings are given for illustrative purposes only and are not meant to be limiting.

Figure 1:
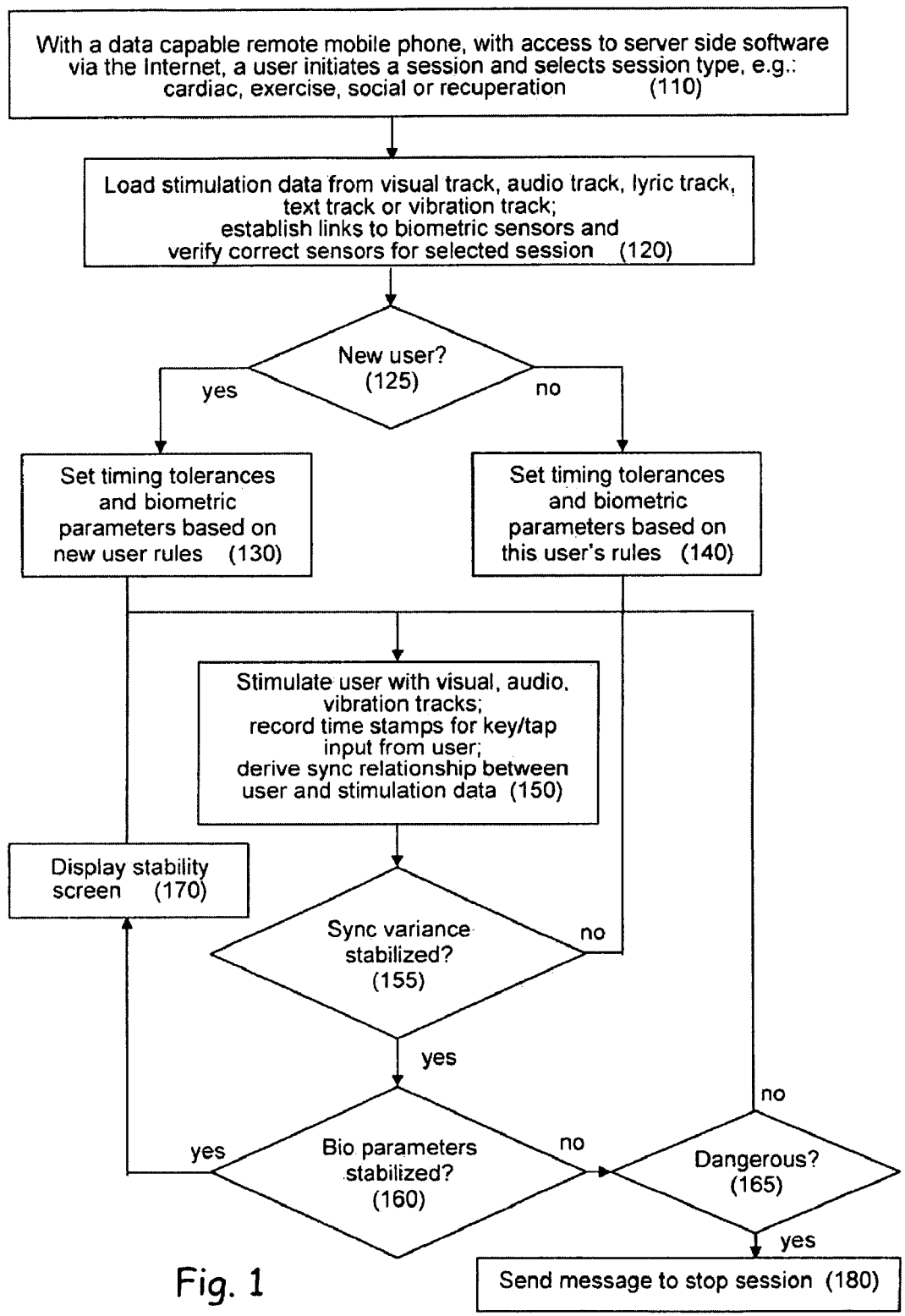
FIG. 1 is a flow chart of a method that allows a user to establish and stabilize his mental, emotional and physical condition, and once this has been achieved to provide for remote or local gathering of standardized biometric data for the user, performed according to the principles of the present invention.

FIG. 1 is a flow chart of a method that allows a user to establish and stabilize his mental, emotional and physical condition, and once this has been achieved to provide for remote or local gathering of standardized biometric data for the user, performed according to the principles of the present invention. With a data capable remote mobile phone, having access to server side software via the Internet, a user initiates a session and selects a session type, e.g., cardiac, exercise, social or recuperation 110. A track is loaded with the stimulation data, which could be a visual, audio, lyrics, text or a vibration track. Links are established to the biometric sensors and it is verified that these are the correct sensors for the selected session 120.

If this is a new user 125, set the timing tolerances and biometric parameters based on new user rules 130. If this is not a new user 125, set the timing tolerances and biometric parameters based on this user's rules 140. Stimulate the user with visual, audio, lyrics, text and/or vibration tracks. Record the time stamps for key/tap input from the user and derive the sync relationship between the user and the stimulation data 150.

If the sync variance 155 and the biometric parameters 160 are stabilized 155, display the stability screen 170. If the biometric parameters are not stabilized 160 and the situation is dangerous 165, send a message to stop the session and send out the proper alerts 180.

In an alternative embodiment the present invention can identify temporal tastes in music, e.g., what a user likes in the morning vs. the music he enjoys in the evening. Location base taste in music can also be recognized. Using GPS, cell tower triangulation, etc., and so on, the present invention can recognize what music may be preferred in a particular location. Combining these time and place features, the present invention can offer a new service: music recommendations based on this information and other available information, similar to the promotions provided by Amazon.com.

For example, "People who listen to music similar to your tastes in the morning also liked to listen to:

| Artist | Track | Album | Label |
|---|---|---|---|
| June Carter | Big Iron | June Carter Live Recordings From The Louisiana Hayride | Scena | music track (click here to obtain it) . . . " . . . or . . . .

"People who listen to your kind of music in this ZIP code also like to eat at "The Top of the Sixes" restaurant . . . " The present invention knows where the user eats from the location based information. The present invention knows where the user is, what time it is and to what music he likes to listen. People with similar taste in music might have similar taste in food or other entertainment.

The present invention will have a database of the lyrics of perhaps a majority of the songs in the world, hopefully translated into English at least, with a search capability on the lyrics database. For example, one can search for songs with the words: cherry blossom, Margaret, Guns, broken heart: and rank the results according to: first: all 4 found by frequency of occurrence; 3 found by frequency of occurrence, etc. The present invention can give the list of songs and also the timing where each of the particular lyrics appear. The user can request to hear, for example, only the 30 second around the particular lyrics, by pointing to the time scale at the right time.

There is a common problem when selecting music. One has to wait while the opening bars of the song are played before hearing the song words. Observing people searching on iTunes or Amazon, for example, a selection is not usually made until the song lyrics have started to be sung. According to a preferred embodiment of the present invention, by accessing the derived start point of the singing of the lyrics, a user can audition songs quickly by playing from the start of the sung lyrics sync point. One may also use any of the other lyric line start points to start the audition from before purchase selection.

A further enhancement for song selection can be achieved by integrating a thesaurus and or phrase/grammar database engine into a song search engine enhanced by the present invention. Obviously this would allow a user to find all songs in the database with a phrase such as 'My beautiful Chinese Doll.' By playing each song from the start point of the line that included the searched-for-phrase a user can quickly find and select a song or songs containing the desired phrase.

By integrating a text based translation engine, the search can be further enhanced. Again, taking the 'My beautiful Chinese Doll' example, a user can also find all Chinese songs whose lyrics contain such a phrase or a similar phrase, but sung in Chinese. The user can then quickly audition the songs as outlined above with the song being played from the point in the song where the lyric line includes the desired phrase or words. The search phrase can also be highlighted by way of color or font style, etc. as the present invention plays the lyrics and song simultaneously as outlined earlier. The invention also allows for the simultaneous display of a song's lyrics in more than one language.

A further usage of the sync data enables a mobile user to extract a segment of a media stream easily and quickly. For example, in Bohemeian Raphsody a user might mark a lyric line for extraction: fourth verse. The user, while watching and listening on a mobile phone, by way of illustration, marks the lyric line 'Galileo, Galileo' for extraction.

"I see a little silhouette of a man,
Scaramouche, scaramouche will you do the fandango—
Thunderbolt and lightning—very very frightening me—
Galileo, galileo,
Galileo, galileo,
Galileo figaro—magnifico—
But I'm just a poor boy and nobody loves me—
He's just a poor boy from a poor family—
Spare him his life from this monstrosity—"

The server extracts the music/video segment by using the sync point for the start of the marked lyric line as the start point for the extraction of data and the sync point of the start of the next lyric line as the end point for the extraction of data. The extracted data can then be sent to the user. The could be used in many ways. For example, it could be used as an identifier tag for the user in social networks such as Facebook and myspace or it could be emailed to friends or used as a ring tone. Alternatively, the server could use the identity of the user and his profile on TuneWiki to track such lyric edits as he might make and then when requested by the user the server would just serve the specific extracted data as identified by the sync point. The advantage of this approach is that it enables auditing usage and the control of downloading media and any derivative copyright that might persist after extraction from the source data.

Figure 2:
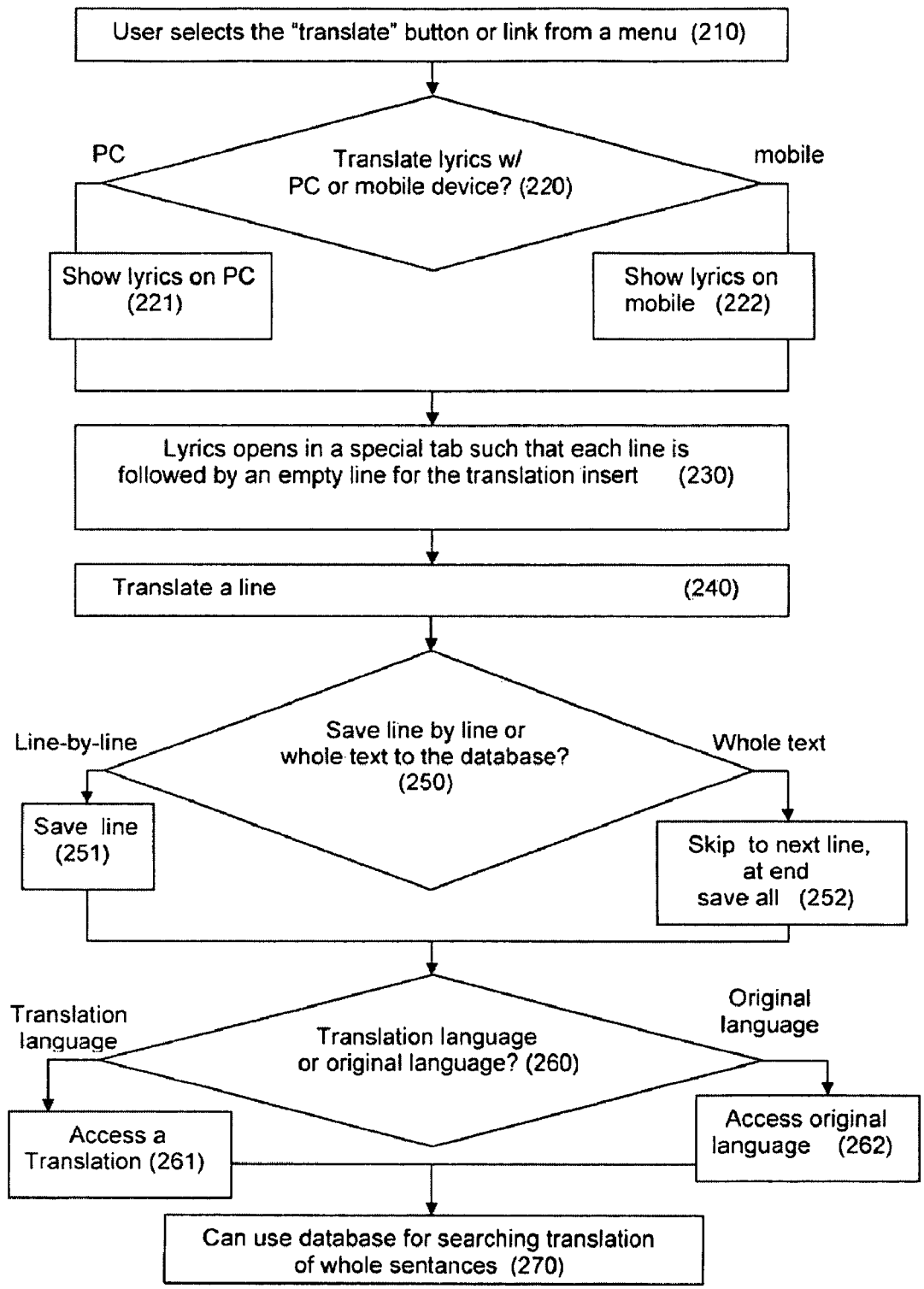
FIG. 2 is a flowchart for a method to translate text subtitles, of which lyrics is one example, from one language to another, performed according to the principles of the present invention.

FIG. 2 illustrates another alternative embodiment. FIG. 2 is a flowchart for a method to translate text subtitles, of which lyrics is one example, from one language to another, performed according to the principles of the present invention. From a menu, the user can select the "translate" button, or a link 210, for example. The user decides whether to translate lyrics using a PC or a mobile phone 220, although someone skilled in the art will know of many other devices for this purpose. The lyrics, or other text will be opened in a special tab in such a way that each line is followed by an empty line for the translation insert 230:

For example:
The lyrics would be:
"Ground control to major Tom
Check ignition
And may god love's be with you."
Would be presented on the screen as:
"Ground control to major Tom" Choose translation language: [from a list]
_____ Insert translation
"Check Ignition"
_____ Insert Translation
"And may god love's be with you"
_____ Insert Translation Each line is translated accordingly by the user 240. The user decides 250 whether to save the lyrics line-by-line 251 or to save a screenful or the whole text at the end of the translation 252. Subsequently, when the user is shown the text, he would be able to choose 260 a translation language 261 or the original language of the text 262. If there are translations into several languages the user can choose among these from a scrollable list. The user can subsequently utilize the resulting database of translated material for searching translations of whole sentences 270.

The user can search for a specific word in the lyrics of a video or audio file and receive the exact location in the video or audio file.

In a video embodiment, the present invention enables users to add lyrics to any video file and synchronize the lyrics, by applying a time stamp, either by clicking with a mouse or by clicking on the screen of a PC or a hand held unit. Lyrics and the time stamps can be used to search for audios and/or videos that include the synchronized lyrics, for example:

Find all the files that include the word "Jasmine:"
Results can be shown as follows:
Video 1—My flower "Jasmine"—time mentioned 1:24 min—click to see exact quote—click to see whole video; and
Audio 4—"Jasmine" my love is as gentle as a flower—time mentioned 2:45 min—click to hear exact quote—click to hear whole audio.

Such a database can be built manually by users or automatically by a computer. The database enables users to search video and audio files by the actual lyric content in them.

In still another alternative embodiment the user can download a synched lyrics file in order to look at the lyrics. The user may be listening to the radio or other source of an audio file that is not in his handheld device, such as his mobile phone. He can scroll the downloaded lyrics manually to the exact point, and then hit a play lyrics button that will start to scroll the lyrics automatically according to the time stamps, even though the audio file is not in the user's device.

Furthermore, the software of the present invention may use any third party software or proprietary automatic identification software that identified the audio file and the exact point in the song, and then match it with the time stamps and show the lyrics exactly at the right point and allow automatic scrolling.

For example: A user listens to a song in the radio. The user then activates the software that identifies the song name and the artist and the exact time on the song. Then the software downloads the lyrics from the database and starts to display the lyrics at the same time stamp identified by the identification software.

In one more alternative embodiment the present invention uses automatic detection of lyrics timing as follows:
1) An audio file of the song is available on the user's mobile phone, for example;
2) A text file of the lyrics is also available, again on the user's exemplary mobile phone; and
3) The present invention can use known speech to lyrics technology to generate a text file, wherein by knowing each word in advance, once the word is detected, a timing file can be generated.

A graphic Equalizer, more commonly known as an EQ is used to change the frequency response, or in other words the tone of a song. It can be used to give more bass, less bass, more treble . . . etc. Just as on a stereo, one can adjust the relative volumes of low and high-frequency sounds by moving the low-EQ and hi-EQ sliders. In yet one more alternative embodiment EQ wiki enables users to EQ a song and share the EQ commands with others. This embodiment provides a synchronization method of one word at a time. The method enables the user to run his finger on the touch screen of an iPhone, for example, while the song is playing. The synchronizing finger 'run' of the user is recorded, and when played back, the present invention can highlight the words or show the temporal "smear" of the synchronizers' finger.

Having described the present invention with regard to certain specific embodiments thereof, it is to be understood that the description is not meant as a limitation, since further modifications will now suggest themselves to those skilled in the art, and it is intended to cover such modifications as fall within the scope of the appended claims.

We claim:

1. A method enabling a user with an electronic communication device to establish and stabilize his mental, emotional and physical condition in response to stimulation data and then using biometric sensors applied to the user to provide for at least one of remote and local gathering of standardized biometric data into a remote database coordinated with remote server software via an electronic network, said method comprising:
    initiating a session and selecting a session type by the user;
    loading a track with the stimulation data;
    establishing links to the biometric sensors;
    setting the timing tolerances and biometric parameters based on one of: new user rules; and existing user's rules if previously acquired;
    stimulating the user with at least one of visual, audio, lyrics, text and vibration tracks to elicit stimulation data from the user;
    recording time stamps corresponding to key/tap input from the user;
    deriving the sync relationship between the user and the stimulation data;
    waiting for any sync variance and said biometric parameters to stabilize; and
    displaying a depiction of the stabilized condition on the screen of the user's electronic communication device.

2. The method according to claim 1, wherein said session type is at least one of cardiac, exercise, social and recuperation.

3. The method according to claim 1, wherein said stimulation data comprises a track of at least one of visual, audio, lyrics, text and vibration data.

4. The method according to claim 1, wherein said electronic network is the Internet.

5. The method according to claim 1, wherein said electronic communication device is a mobile phone.

6. The method according to claim 1, further comprising verifying that said biometric sensors in the establishing step are the correct sensors for the selected session.

7. The method according to claim 1, wherein if the biometric parameters indicate the situation is dangerous, said method further comprising sending a message to stop the session and sending out the proper alerts.

* * * * *